United States Patent
Nativ et al.

(10) Patent No.: US 11,826,028 B2
(45) Date of Patent: Nov. 28, 2023

(54) TWO COMPONENT SEALING SYSTEMS INCLUDING SYNTHETIC MATRICES AND BIOSYNTHETIC ADHESIVES FOR SEALING RESECTED SURFACES OF ORGANS TO CONTROL BLEEDING, FLUID LEAKS AND AIR LEAKS

(71) Applicant: Ethicon, Inc., Somerville, NJ (US)

(72) Inventors: Nir Nativ, West Orange, NJ (US); Sridevi Dhanaraj, Raritan, NJ (US); Ashley DeAnglis, Skillman, NJ (US); Salim Ghodbane, Piscataway, NJ (US)

(73) Assignee: Ethicon, Inc., Somerville, NJ (US)

( * ) Notice: Subject to any disclaimer, the term of this patent is extended or adjusted under 35 U.S.C. 154(b) by 305 days.

(21) Appl. No.: 16/897,328

(22) Filed: Jun. 10, 2020

(65) Prior Publication Data
US 2021/0393245 A1     Dec. 23, 2021

(51) Int. Cl.
*A61B 17/00*      (2006.01)
*A61L 24/10*      (2006.01)
(Continued)

(52) U.S. Cl.
CPC .......... *A61B 17/0057* (2013.01); *A61L 24/10* (2013.01); *A61L 31/005* (2013.01);
(Continued)

(58) Field of Classification Search
CPC ........ A61B 17/00491; A61B 17/00513; A61B 17/0057; A61B 17/08; A61B 17/085;
(Continued)

(56) References Cited

U.S. PATENT DOCUMENTS 5,593,441 A * 1/1997 Lichtenstein ......... A61F 2/0063
623/23.72
5,686,090 A * 11/1997 Schilder ................ A61L 31/148
424/422
(Continued)

FOREIGN PATENT DOCUMENTS

EP         0669138        8/1995
WO       2006014581        2/2006
(Continued)

OTHER PUBLICATIONS

Sargeant, Timothy D. et al., "An in situ forming collagen-PEG hydrogel for tissue regeneration," Acta Biomaterialia, Jan. 2012, pp. 124-132, vol. 8, Issue 1, Research and Development, Surgical Devices, Covidien LLC, 60 Middletown Avenue, North Haven, CT 06473, USA.

(Continued)

*Primary Examiner* — Ryan J. Severson
(74) *Attorney, Agent, or Firm* — Troutman Pepper Hamilton Sanders LLP

(57) ABSTRACT

A method of sealing a resected surface of an organ includes applying a synthetic matrix to a resected surface of an organ, and applying an adhesive on the synthetic matrix so that the adhesive penetrates through interstices of the synthetic matrix for contacting an interface between the synthetic matrix and the resected surface of the organ. The method includes curing the adhesive for bonding the synthetic matrix to the resected surface of the organ. The synthetic matrix is a non-woven mesh made of polyglactin 910 or any other synthetic or non-synthetic fabric having a similar porosity or density. The adhesive is a biosynthetic or a synthetic adhesive. After penetrating through the pores of the synthetic matrix and curing, the cured biosynthetic or synthetic adhesive mechanically interlocks with the syn- (Continued)

thetic matrix for adhering the synthetic matrix to the tissue for creating a sealing barrier.

23 Claims, 11 Drawing Sheets

(51) Int. Cl.
| | |
|---|---|
| *A61L 31/00* | (2006.01) |
| *A61L 31/04* | (2006.01) |
| *A61L 31/12* | (2006.01) |
| *A61L 31/14* | (2006.01) |
| *A61L 31/06* | (2006.01) |

(52) U.S. Cl.
CPC .............. *A61L 31/047* (2013.01); *A61L 31/06* (2013.01); *A61L 31/125* (2013.01); *A61L 31/146* (2013.01); *A61L 31/148* (2013.01); *A61B 2017/00004* (2013.01); *A61B 2017/0065* (2013.01); *A61L 2400/04* (2013.01)

(58) Field of Classification Search
CPC .......... A61B 2017/00004; A61B 2017/00504; A61B 2017/0065; A61B 2017/00884; A61B 2017/081; A61L 31/047; A61L 31/06; A61L 31/146; A61L 2400/04; A61F 2/0063; A61F 2002/0068; A61F 2002/0077; A61F 2002/0086; A61F 2013/00655

See application file for complete search history.

(56) References Cited

U.S. PATENT DOCUMENTS

| | | | | |
|---|---|---|---|---|
| 5,874,500 | A * | 2/1999 | Rhee ....................... | A61L 24/08 525/425 |
| 6,051,648 | A * | 4/2000 | Rhee ................... | C08B 37/0075 525/425 |
| 6,166,130 | A * | 12/2000 | Rhee ..................... | A61L 31/041 525/425 |
| 8,043,629 | B2 | 10/2011 | Uchida et al. | |
| 8,962,025 | B2 * | 2/2015 | Rhee ....................... | A61K 47/42 424/491 |
| 10,206,686 | B2 * | 2/2019 | Swayze ............ | A61B 17/12181 |
| 2001/0003126 | A1 * | 6/2001 | Rhee ..................... | A61L 24/043 525/425 |
| 2002/0013408 | A1 * | 1/2002 | Rhee ....................... | A61L 27/34 525/54.1 |
| 2003/0119985 | A1 * | 6/2003 | Sehl ........................ | C08H 1/06 525/54.1 |
| 2003/0149173 | A1 * | 8/2003 | Rhee ....................... | C08H 1/00 525/54.1 |
| 2004/0185084 | A1 * | 9/2004 | Rhee ....................... | A61L 31/16 427/2.24 |
| 2004/0186230 | A1 * | 9/2004 | Rhee ....................... | C08H 1/06 525/425 |
| 2004/0186231 | A1 * | 9/2004 | Rhee ....................... | C08L 71/02 525/54.3 |
| 2004/0187877 | A1 | 9/2004 | Badylak et al. | |
| 2004/0235708 | A1 * | 11/2004 | Rhee ....................... | C08L 71/02 514/579 |
| 2005/0027069 | A1 * | 2/2005 | Rhee ....................... | A61L 27/54 525/54.1 |
| 2005/0027070 | A1 * | 2/2005 | Rhee ....................... | C08L 71/02 525/403 |
| 2005/0054771 | A1 * | 3/2005 | Sehl ........................ | C09J 189/06 525/54.1 |
| 2005/0159544 | A1 * | 7/2005 | Rhee ....................... | A61L 27/54 525/54.1 |
| 2006/0257458 | A1 * | 11/2006 | Gorman ................... | B32B 23/02 424/445 |
| 2007/0154509 | A1 * | 7/2007 | Wilcher ................... | A61L 15/18 424/422 |
| 2007/0208134 | A1 * | 9/2007 | Hunter ............... | A61K 47/6957 525/54.1 |
| 2009/0156711 | A1 * | 6/2009 | Van Holten ............. | A61L 15/38 523/118 |
| 2010/0233246 | A1 * | 9/2010 | Sehl ........................ | C08L 71/02 424/443 |
| 2010/0286791 | A1 * | 11/2010 | Goldsmith ........ | A61B 17/12022 604/524 |
| 2011/0195040 | A1 * | 8/2011 | Rhee ................... | C08B 37/0075 424/78.3 |
| 2011/0280919 | A1 * | 11/2011 | Moloye-Olabisi ... | A61K 38/363 424/94.64 |
| 2012/0209319 | A1 | 8/2012 | Bianco-Peled et al. | |
| 2012/0276150 | A1 | 11/2012 | Lauritzen et al. | |
| 2012/0315316 | A1 * | 12/2012 | Moloye-Olabisi ...... | A61P 17/02 424/94.64 |
| 2015/0045455 | A1 * | 2/2015 | Mcarthur ................. | A61L 24/06 514/772 |
| 2015/0351776 | A1 * | 12/2015 | Swayze ............ | A61B 17/12177 600/249 |
| 2018/0243481 | A1 * | 8/2018 | Martin .................... | A61L 27/56 |
| 2019/0125936 | A1 * | 5/2019 | Preiss-Bloom ........ | A61L 31/146 |
| 2021/0393245 | A1 * | 12/2021 | Nativ ...................... | A61L 24/10 |

FOREIGN PATENT DOCUMENTS

| | | |
|---|---|---|
| WO | 2010/146582 A2 | 12/2010 |
| WO | 2017/195198 A1 | 11/2017 |

OTHER PUBLICATIONS

Hong Yi et al., "A strongly adhesive hemostatic hydrogel for the repair of arterial and heart bleeds," Nature Communications, 2019, pp. 1-11, vol. 10:2060.

Richardson Peter D. I. et al., "Liver Blood Flow. I. Intrinsic and Nervous Control of Liver Blood Flow," Gastroenterology, 1981, vol. 81, pp. 159-173.

International Search Report and Written Opinion dated Sep. 1, 2021, from corresponding International Application No. PCTIB2021054988.

* cited by examiner

TWO COMPONENT SEALING SYSTEMS INCLUDING SYNTHETIC MATRICES AND BIOSYNTHETIC ADHESIVES FOR SEALING RESECTED SURFACES OF ORGANS TO CONTROL BLEEDING, FLUID LEAKS AND AIR LEAKS

BACKGROUND OF THE INVENTION

Field of the Invention

The present patent application is generally related to surgical procedures, and is more specifically related to systems, devices and methods for sealing the resected surfaces of tissue and organs to manage bleeding, fluid leaks, and air leaks.

Description of the Related Art

A resection is a surgical procedure that involves cutting out tissue or a part of an organ. Resections, which are performed on a wide variety of organs including livers, lungs and gastrointestinal systems, present surgeons with many unique problems related to effectively managing post-operative bleeding, and fluid and air leaks.

During organ resection procedures, surgeons manage major bleeding at resected surfaces by using tourniquets, extensive suturing, etc. Some surgeons use adhesive fluids (e.g., synthetic adhesives, fibrin glue gels), which are limited since they can flow off the resected surface prior to completely curing or can peel off easy following curing since they lack adequate adherence to underlying tissue or proper elastic properties.

Liver Resection. A surgical procedure that involves removing all or part of a liver is commonly referred to as a hepatectomy. A partial hepatectomy is a preferred approach for removing a solid tumor from a liver. During resection of a liver, the tissue margins within the resected area are destroyed and the internal parenchyma and flow systems are exposed. The re-establishment of proper margins does not occur immediately, but requires an extended tissue healing process that can last from days to weeks. During the tissue healing process, the resected tissue can ooze blood and/or leak organ specific liquids (e.g., bile), which can cause post-operative complications. One study found that after liver resection procedures, the bile leakage rate was about 5%, which dramatically increased the likelihood of patient post-operative complications.

Lung Resection. Lung resection procedures typically require a significant amount of tissue manipulation and handling, which results in a high incidence of post operative air leaks. Standardized techniques that are used to address air leaks involve suturing or stapling the lung tissue. These techniques are often ineffective, however, in creating an airtight seal due to the intrinsic friability of the lung parenchyma, particularly in emphysematous patients. In some instances, topical adhesives are applied either directly on the pleural abrasion or onto staple lines, however, these techniques are often inadequate for preventing air leaks.

GI Resection. Gastrointestinal (GI) procedures often involve excising large segments of a patient's intestinal anatomy for effectively treating disease. After removing GI tissue, surgeons are required to reconstruct the patient's digestive system. GI reconstructions are complicated due to the delicate structure of the intestines, limited blood supply to lower colon, limited surgeon access to complex anatomical structures, and the pathologies that typically affect the surrounding tissues. Even when surgeons exercise great care during GI reconstruction procedures, however, there are a certain percentage of patients who will have complications resulting from leaks at surgically created anastomotic sites. GI leaks can result in devastating outcomes, requiring additional surgeries and treatments that are often unsuccessful in managing the leaks.

In view of the above-noted complications, there have been many efforts directed to effectively managing intra and post-operative bleeding, and fluid and air leaks. For example, when resecting solid organs, surgeons typically manage major bleeding at resected surfaces by using tourniquets and extensive suturing. Minor bleeding and fluid leakage is often managed by using adhesive fluids (e.g., synthetic adhesives, fibrin glue) to cover the resected surfaces, however, these methodologies have achieved limited success because the adhesive fluids tend to flow off of the resected surfaces prior to curing and/or peel off after curing because the cured adhesive lacks adequate adherence to underlying tissue or proper elastic properties.

Covidien sells a VERISET® hemostatic patch for sealing resected tissue surfaces. The VERISET® hemostatic patch is composed of an oxidized regenerated cellulose (ORC) layer and a reactive polyethylene glycol (PEG) layer. The patch is applied to a tissue surface by applying pressure on the surface. Due to the fact that the OR® matrix is opaque, while applying pressure onto the resected surface, a surgeon cannot see through the VERISET® hemostatic patch to assess the condition of the resected surface. The patch is also rigid with low flexibility and therefore may not achieve good tissue conformability or remain compliant with tissue movements.

In view of the above-noted deficiencies, there is a continuing need for improved systems, devices and methods that enable surgeons to effectively seal resected surfaces of organ and tissue, and to prevent and/or successfully manage intra and post-operative bleeding, fluid leaks and/or air leaks from resected surfaces of tissue and organs.

To date, there have been many efforts directed to sealing the resected surfaces of organs to manage intra and post-operative bleeding, fluid leakage, and air leakage. Some of these efforts involve applying a mesh to a resected surface, followed by applying fibrin glue to seal the resected surface. Animal model experiments, however, indicate that fibrin glue does not have the tissue bonding strength to adhere the mesh to a resected surface of an organ.

SUMMARY OF THE INVENTION

The present patent application discloses preferred systems, devices and methods for overcoming the above-identified deficiencies and effectively sealing resected surfaces to control bleeding, fluid leaks, and air leaks.

In one embodiment, the systems, devices and methods include using two component sealant that may be applied to the resected surfaces of soft organs (e.g., liver, lung, GI system, pancreas) in order to control intra and post-operative bleeding, fluid leaks (e.g., bile leaks), and/or air leaks.

In one embodiment, the first component of the two component sealant may be a synthetic matrix (e.g., mesh or non-woven) that is placed on a resected surface of an organ. In one embodiment, the synthetic matrix is a non-woven matrix. In one embodiment, the synthetic matrix is a biodegradable synthetic matrix.

In one embodiment, the synthetic matrix may be a synthetic substrate or patch such as an absorbable synthetic substrate made of a polyglactin 910 (PG910) material that is manufactured and sold under the trademark VICRYL® polyglactin 910 material by Ethicon, Inc. of Somerville, N.J. In one embodiment, the polyglactin 910 material may include 90% glycolide and 10% L-lactide.

In one embodiment, the synthetic matrix that may be placed on the resected surface of an organ together with the second component of the two component sealant, which may be a biosynthetic adhesive in a liquid or powder form (e.g., an albumin and PEG-SG mixture).

In one embodiment, the synthetic matrix may be a flexible or conformable non-woven matrix that is adapted to be placed onto the resected surface of an organ and conform to the shape of the resected surface and/or the organ. In one embodiment, the synthetic matrix is bioabsorbable.

In one embodiment, the density of the synthetic matrix may be tailored to maximize the adhesiveness and cohesiveness of the sealant to form a non-permeable mechanical barrier. The adhesiveness and cohesiveness are preferably assessed together by analyzing the system's ability to withstand normal pressure that is applied to a surface of the synthetic matrix.

In one embodiment, the second component of the two component sealant may be an adhesive such as a biosynthetic adhesive or a synthetic adhesive. The adhesive may be in a liquid or a powder form.

In one embodiment, the adhesive may include a biocompatible, reactive electrophile and a nucleophile. In one embodiment, the electrophile may include PEG-SG. In one embodiment, the nucleophile may be selected from any source of amine ($NH_2$) groups (e.g., primary amine moieties), any appropriate protein or protein mixture, albumin, polyethylene glycol amines (PEG-$NH_2$), and combinations of albumin and PEG-N $H_2$.

In one embodiment, the biosynthetic adhesive may be a solution of protein (e.g., Albumin) or partially hydrolyzed protein (e.g., Peptone) and polyethylene glycol succinimidyl glutarate (i.e., PEG-SG).

In the present patent application, the term adhesive means a biosynthetic or synthetic adhesive in liquid or power form that is used to adhere a synthetic matrix (i.e., an absorbable synthetic substrate made of polyglactin 910) to tissue (e.g., a resected surface of an organ).

In the present patent application the term sealant or sealing device means a combination of a synthetic matrix and a biosynthetic or synthetic adhesive in liquid or power form that is used to adhere the synthetic matrix to tissue.

As will be set forth in more detail herein, it has been determined that the unique fiber architecture of the non-woven PG910 matrix provides proper support for the biosynthetic or synthetic adhesive to cure in a manner that will form a superior level of adhesion for forming a fluid and/or air-tight seal.

As will be disclosed in more detail herein, the order in which the first and second components are applied to resected surfaces, as well as the particular composition of the biosynthetic adhesive, may affect the efficacy of the sealant, and thus can be modified and/or tailored for effective use on a specific organ or particular application.

In one embodiment, the synthetic matrix or nonwoven matrix and the biosynthetic or synthetic adhesive may be applied in different forms and using different methods in order to control leaks including but not limited to bleeding and fluid leaks from resected organs (e.g., liver, GI system) and/or air leaks from resected lungs.

In one embodiment, the biosynthetic or synthetic adhesive is applied to a biodegradable synthetic matrix (e.g., VICRYL® non-woven PG910), which is placed on a resected surface of an organ. The biosynthetic adhesive may be a solution of protein or partially hydrolyzed protein (e.g., albumin) and polyethylene glycol succinimidyl glutarate (PEG-SG) that is pre-mixed immediately prior to use.

In one embodiment, the density of the synthetic matrix is controlled (i.e., optimized) to ensure that the biosynthetic adhesive is retained by the synthetic matrix.

In one embodiment, the density of the synthetic matrix is controlled (i.e., optimized) to ensure that the biosynthetic adhesive fully permeates through the thickness of the synthetic matrix for contacting the resected surface and forming a liquid and/or air-tight seal over the resected surface.

In one embodiment, the two component sealant is allowed a period of time (e.g., 30 seconds to five minutes) for adhering to the resected tissue, whereupon the synthetic matrix and biosynthetic or synthetic adhesive combination preferably form a seal at the resected surface to prevent bleeding, fluid leaks (e.g., bile), and/or air leaks.

In one embodiment, the biosynthetic adhesive may be applied to the surface of the synthetic matrix that faces away from the resected surface of the tissue.

In one embodiment, the density of the matrix may be modified and/or optimized for maximizing the cohesiveness resulting from the combination of the synthetic matrix and the biosynthetic adhesive. In one embodiment, to allow the biosynthetic adhesive to permeate through the synthetic matrix to achieve adherence to the underlying tissue, the density of the matrix is optimized (e.g., made sufficiently low enough) to allow the biosynthetic or synthetic adhesive to penetrate through the matrix and reach the tissue surface, whereupon the biosynthetic adhesive may cross-link with the surface molecules of the tissue. In one embodiment, full penetration of the biosynthetic adhesive into the interstices of the matrix desirably forms a cohesive, cross-linked hydrogel, which incorporates the matrix fibers that serve as a reinforcement scaffold.

In one embodiment, the density of the synthetic matrix is preferably optimized to enhance the ability of the synthetic matrix to retain the biosynthetic adhesive until the adhesive is cross-linked to optimize cohesive properties. As set forth herein, the ability of the synthetic matrix to retain the biosynthetic adhesive will increase with increasing matrix density up until a critical point, beyond which the synthetic matrix becomes too dense to allow for sufficient penetration of the biosynthetic adhesive through the synthetic matrix and retention of the biosynthetic matrix by the synthetic matrix.

In one embodiment, the systems, devices and methods disclosed herein provide an optimal matrix density range for a synthetic matrix, whereby the optical matrix density range is utilized for 1) maximizing penetration of the biosynthetic adhesive through the matrix, 2) maximizing retention of the biosynthetic adhesive by the matrix, 3) maximizing the system's ability to withstand pressure applied to the matrix, 4) maximizing the functionality of the two component sealant to stop bleeding and seal fluid and air leaks, and 5) maximize the device conformability to tissue.

In one embodiment, a method of sealing or providing hemostasis to an organ or a wound preferably includes applying a porous, flexible, synthetic matrix to the organ or wound, and applying an adhesive (e.g., a biosynthetic or synthetic adhesive, such as by spray) on top of the synthetic matrix, thereby allowing the adhesive to penetrate through the synthetic matrix to reach an interface between the substrate and the organ, wound, or resected surface.

In one embodiment, the method includes curing the adhesive for bonding the synthetic matrix to the organ or wound.

In one embodiment, for soft tissue resection, the porosity of the synthetic matrix preferably has a density range of about 102-191 mg/cm$^3$, and more preferably about 102.7-190.7 mg/cm$^3$, which is suitable for sealing a soft tissue resection.

In one embodiment, for high pressure bleeding, the porosity of the synthetic matrix preferably has a density range of about 128-191 mg/cm$^3$, and more preferably about 128.7-190.7 mg/cm$^3$, which is suitable for sealing high pressure bleeding.

In one embodiment, a method of sealing a resected surface of an organ to prevent bleeding, fluid leaks and/or air leaks preferably includes applying a synthetic matrix to a resected surface of an organ, applying an adhesive, such as a biosynthetic or synthetic adhesive, on the synthetic matrix so that the adhesive penetrates through interstices of the synthetic matrix for contacting an interface between the synthetic matrix and the resected surface of the organ, and curing the adhesive for bonding the synthetic matrix to the resected surface of the organ.

In one embodiment; the synthetic matrix is a biodegradable, porous, flexible substrate.

In one embodiment, the synthetic matrix is a non-woven mesh made of polyglactin 910.

In one embodiment, the synthetic matrix and the adhesive are preferably at least partially transparent for enabling a surgeon to see through the synthetic matrix during positioning and/or re-positioning of the synthetic matrix on a resected surface of an organ.

In one embodiment, when used for sealing a soft tissue resection, the synthetic matrix preferably has a density range of 102-191 mg/cm$^3$, and more preferably 102.7-190.7 mg/cm$^3$.

In one embodiment, the biosynthetic adhesive desirably includes a partially hydrolyzed protein (e.g., albumin) and polyethylene glycol succinimidyl glutarate (PEG-SG).

In one embodiment, the biosynthetic adhesive may be a mixture of a 10% albumin solution and 75 mg/ml of PEG-SG solution.

In one embodiment, the biosynthetic adhesive may be in a liquid or a powder form.

In one embodiment, after the biosynthetic or synthetic adhesive is applied to the synthetic matrix and is cured, the adhesive mechanically interlocks with fibers of the synthetic matrix, and preferably chemically cross-links with the fibers of the synthetic matrix.

In one embodiment, a method of sealing a resected surface of an organ preferably includes applying a porous, bioabsorbable synthetic matrix made of polyglactin 910 to a resected surface of the organ, applying an adhesive (e.g., a biosynthetic adhesive including albumin and polyethylene glycol succinimidyl glutarate (PEG-SG)) on the synthetic matrix so that the adhesive penetrates through pores of the synthetic matrix for contacting an interface between the synthetic matrix and the resected surface of the organ, and curing the adhesive for bonding the synthetic matrix to the resected surface of the organ.

In one embodiment, prior to the applying the porous, bioabsorbable synthetic matrix to the resected surface of the organ, the method may include a preliminary step of pre-applying the adhesive on the resected surface of the organ, and then applying the synthetic matrix onto the pre-applied adhesive.

In one embodiment, a kit for sealing a resected surface of an organ preferably includes a synthetic matrix including a non-woven mesh made of polyglactin 910, and an adhesive comprising a biocompatible, reactive electrophile and a nucleophile.

In one embodiment, the adhesive may be a biosynthetic adhesive including a partially hydrolyzed protein, such as albumin, and polyethylene glycol succinimidyl glutarate (PEG-SG).

In one embodiment, the kit may include a dual syringe for dispensing the biosynthetic adhesive. The dual syringe may include a first syringe barrel containing a 20% albumin solution and a second syringe barrel containing a 150 mg/ml of PEG-SG solution. The two components are preferably mixed together upon being dispensed from the dual syringe for forming a curable biosynthetic adhesive or mixed in-situ on the matrix that is applied to tissue.

In one embodiment, a kit for sealing or providing hemostasis to an organ or a wound preferably includes an absorbable synthetic, porous matrix (e.g., a non-woven matrix or patch), such as a VICRYL® non-woven PG910 substrate and a two part adhesive including albumin and PEG-SG.

DETAILED DESCRIPTION OF PREFERRED EMBODIMENTS

In one embodiment, a two component sealant is preferably applied to the resected surfaces of soft organs to prevent intra and post-operative bleeding, fluid leaks (e.g., bile), and/or air leaks (e.g., lungs) from the resected surfaces.

Figure 1:
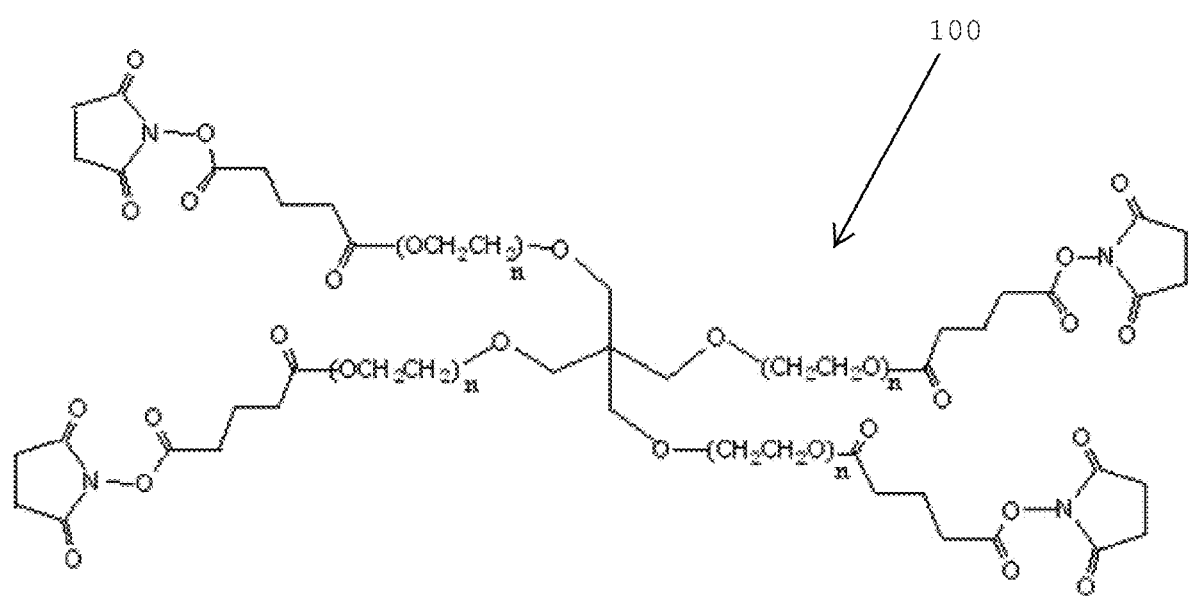
FIG. 1 shows the chemical formula for polyethylene glycol succinimidyl glutarate (PEG-SG) that is a part of a biosynthetic adhesive, in accordance with one embodiment of the present patent application.
Figure 2:
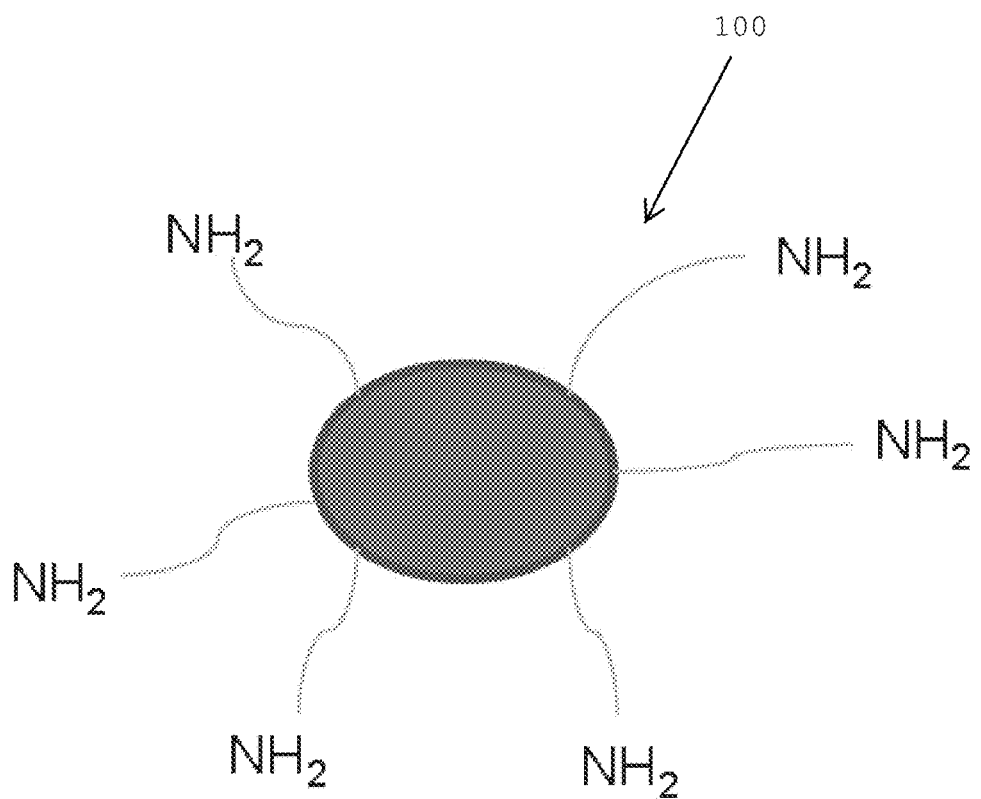
FIG. 2 shows a schematic example of a protein (albumin) that is part of a biosynthetic adhesive, in accordance with one embodiment of the present patent application.

Referring to FIGS. 1 and 2, in one embodiment, a two component sealant for resected surfaces of soft organs preferably includes an adhesive 100, such as a biosynthetic adhesive, that may be applied in a liquid or powder form onto a synthetic matrix. In one embodiment, a biosynthetic adhesive may be a solution that includes a mixture of polyethylene glycol succinimidyl glutarate, also known as PEG-SG, and a protein (e.g., albumin).

Polyethylene glycol succinimidyl glutarate (PEG-SG) has a well-established safety profile in medical devices and has been used in sealant products such as Duraseal and Coseal. The succinimidyl glutarate reacts with amine groups on proteins, e.g., collagen, under mildly alkaline conditions forming an amide bond. The cleavable ester linker designed into the PEG enables the polymer to be degradable in vivo. This form of PEG also provides the ability to cross-link across multiple collagen fibers due to its long spacer region allowing intermolecular cross-linking.

FIG. 1 shows the chemical structure for the polyethylene glycol succinimidyl glutarate (i.e., PEG-SG).

FIG. 2 shows a simplified schematic for the protein (i.e., albumin).

Figure 3:
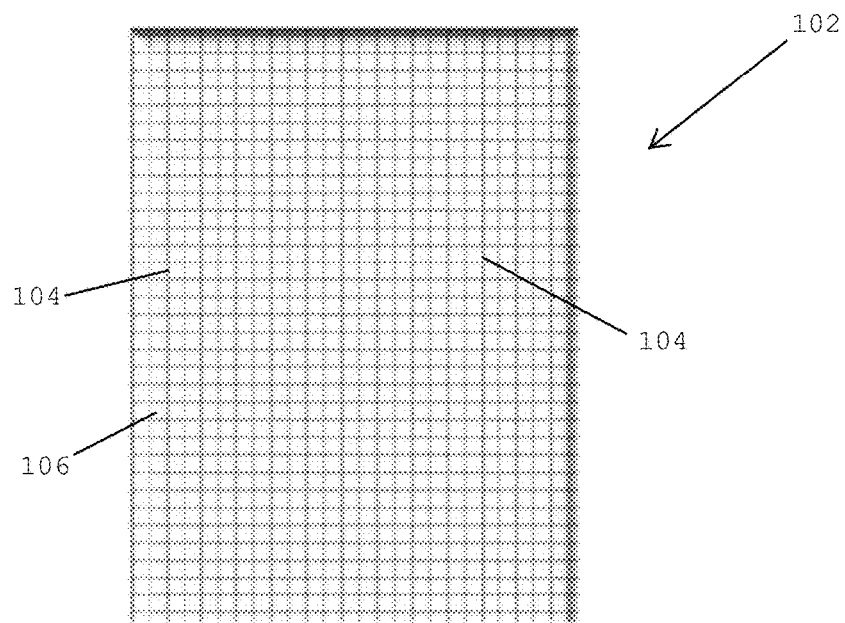
FIG. 3 is a top view of a synthetic matrix, in accordance with one embodiment of the present patent application.

Referring to FIG. 3, in one embodiment, the two component sealant preferably includes a synthetic matrix 102 that is adapted to be placed onto the resected surface of a soft organ. In one embodiment, the synthetic matrix 102 may be a mesh matrix or a non-woven matrix that is placed on the resected surface together with the biosynthetic adhesive 100 (FIGS. 1 and 2). In one embodiment, the non-woven matrix is flexible and/or conformable and is adapted for being placed onto a resected tissue surface, with the biosynthetic adhesive 100 being applied to the synthetic matrix 102.

In one embodiment, the synthetic matrix 102 preferably includes fibers 104 and interstices 106 that are disposed between the fibers 104.

In one embodiment, the biosynthetic adhesive is a cross-linkable liquid adhesive that is applied to the non-woven matrix 102. The biosynthetic adhesive is adapted to permeate through the interstices 106 of the synthetic matrix so that the synthetic matrix 102 will retain the biosynthetic adhesive, whereupon the adhesive will cure and mechanically interlock and/or chemically cross-link with the fibers 104 of the synthetic matrix 102.

In one embodiment, the density of the synthetic matrix 102 may be tailored (i.e., optimized) to maximize the ability of the adhesive to attach to tissue and the cohesiveness of the sealant to form a non-permeable mechanical barrier that covers the resected surface of the organ. In one embodiment, the adhesiveness and cohesiveness may be assessed together by evaluating the system's ability to withstand normal pressure applied to a major surface of the synthetic matrix 102.

Figure 4:
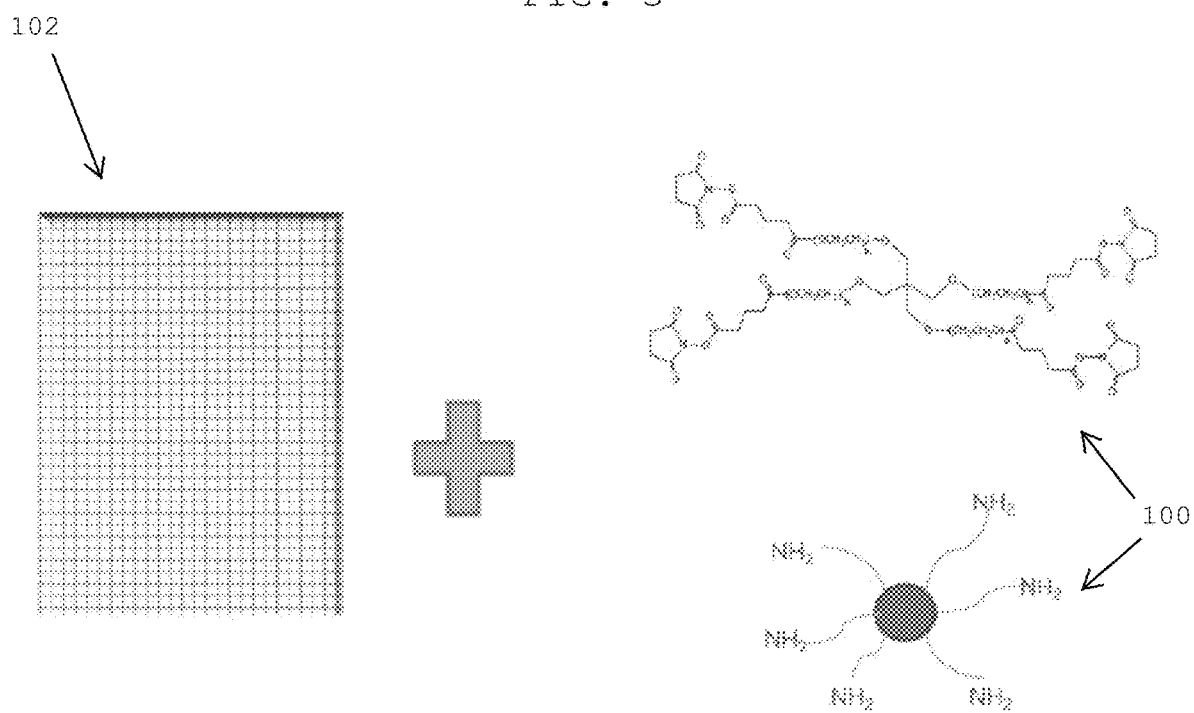
FIG. 4 shows a schematic example of combining a biosynthetic adhesive and a synthetic matrix, in accordance with one embodiment of the present patent application.
Figure 5:
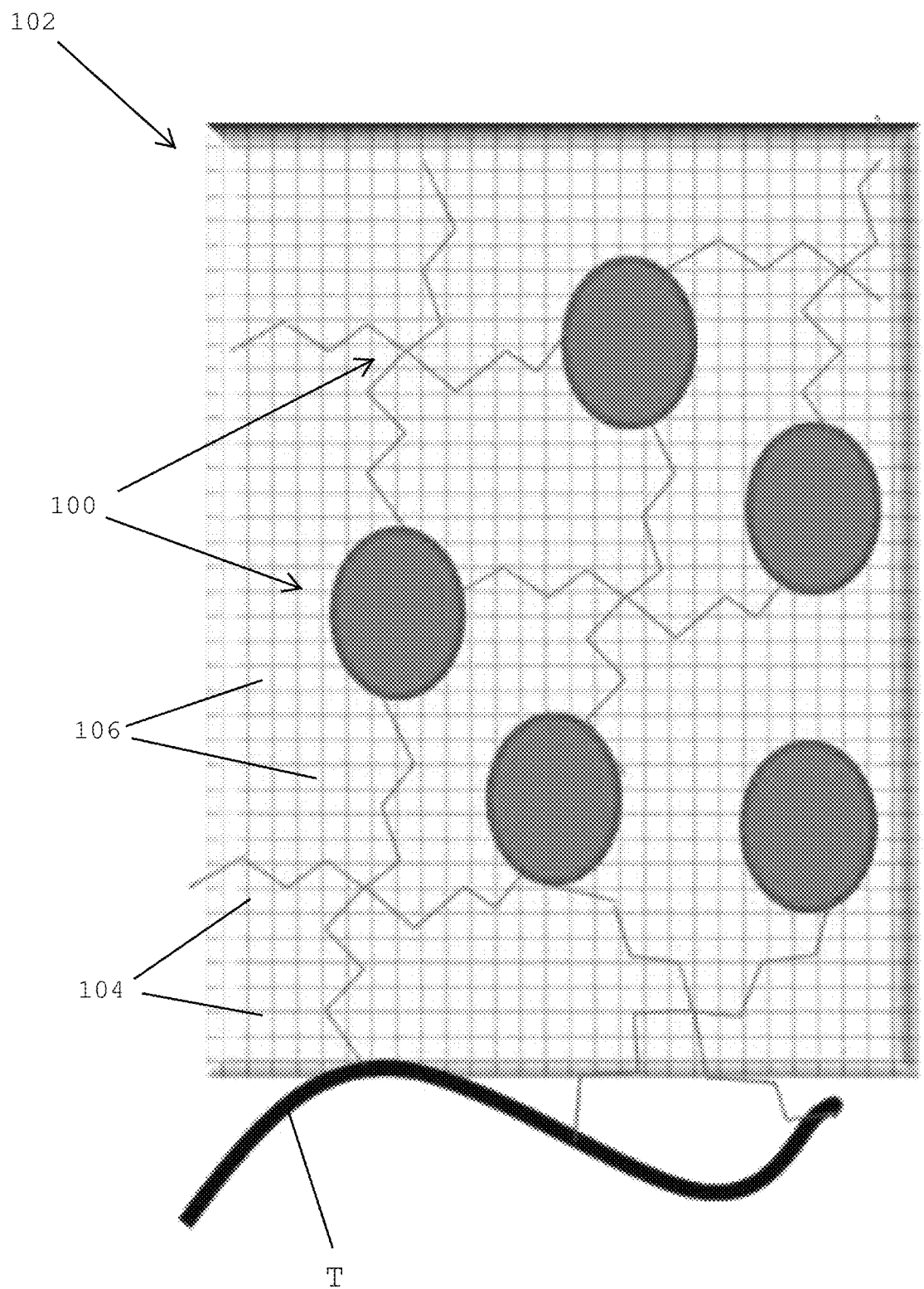
FIG. 5 shows a schematic examples of a biosynthetic adhesive cross-linked with a synthetic matrix for sealing a resected surface of tissue, which is represented by the letter T, in accordance with one embodiment of the present patent application.

Referring to FIGS. 4 and 5, in one embodiment, after the synthetic matrix 102 is applied over a resected surface of tissue T, the biosynthetic adhesive 100 may be applied to the surface of the synthetic matrix 102 that faces away from the resected surface of the tissue T. In one embodiment, the density of the synthetic matrix 102 is selected to be sufficiently low enough to allow the biosynthetic adhesive 100 to penetrate completely through the thickness of the synthetic matrix 102 and reach the resected surface of the tissue, whereupon the biosynthetic adhesive 100 can cure and cross-link with the surface molecules to achieve adhesion to the underlying tissue. In one embodiment, the biosynthetic adhesive 100 is preferably formulated so that it fully penetrates through the interstices of the synthetic matrix 102 to create a cohesive cross-linked hydrogel that incorporates the fibers of the synthetic matrix, which serves as a reinforcement scaffold that seals the resected surface of the tissue T.

In one embodiment, the cohesiveness resulting from the cross-linked hydrogel reinforcement may be increased by controlling the density of the synthetic matrix 102.

In one embodiment, the design parameters for the synthetic matrix 102 are selected to optimize the ability of the synthetic matrix to retain the biosynthetic adhesive 100 for a sufficient period of time to enable the adhesive to cure and mechanically interlock and/or to chemically cross-link with the fibers 104 of the synthetic matrix 102, which, in turn, optimizes the cohesive properties of the two component sealant. The ability of the synthetic matrix to retain the biosynthetic adhesive is preferably increased by increasing the matrix density up to a predetermined density level (i.e., a critical point, an optimized density level). Beyond the predetermined density level, the synthetic matrix will be too dense to allow for sufficient penetration of the biosynthetic adhesive through the thickness of the synthetic matrix and retention of the biosynthetic adhesive by the synthetic matrix.

In one embodiment, the specification and design parameters for the biosynthetic adhesive 100 and the synthetic matrix 102 are established by identifying an optimal matrix density range that maximizes penetration of the biosynthetic adhesive (e.g., a liquid) through the thickness of the synthetic matrix, retention of the biosynthetic adhesive by the synthetic matrix, and the system's ability to withstand pressure resulting from bleeding, fluid leaks, and air leaks, thereby maximizing the functionality of the two component sealant to stop bleeding and seal fluid and air leaks.

In one embodiment, the synthetic matrix (e.g., VICRYL® PG910 mesh) may be functionalized with amine groups to enable formation of covalent bonds between the synthetic matrix and the PEG molecules (i.e., PEG-SG), which will eventually covalently bind the synthetic matrix molecules to the tissue. A protein solution or a partially digested protein may be applied to the synthetic matrix and the resected area as disclosed herein as a PEG-SG substrate to form a sealant.

FIGS. 4 and 5 show the reaction of the PEG-SG4 (4-arm version) with albumin. The amine ($NH_2$) groups of the protein (e.g., primary amine moieties), which are depicted in FIGS. 4 and 5, react with the succinimidyl glutarate of the PEG forming a covalent (amide) bond. The PEG-SG4 is also capable of reacting with proteins on the tissue surface (e.g., collagen), providing adhesion of the cross-linked polymer to the tissue surface.

In one embodiment, an experiment was conducted to determine optimal density levels for synthetic matrices. In one embodiment, five matrices were evaluated, each matrix having a comparable volume but a different density. In one embodiment, a first synthetic matrix specimen (i.e., Matrix 1) had a density of about 93.0 $mg/cm^3$; a second synthetic matrix specimen (i.e., Matrix 2) had a density of about 120.5 $mg/cm^3$; a third synthetic matrix specimen (i.e., Matrix 3) had a density of about 131.2 $mg/cm^3$; a fourth synthetic matrix specimen (i.e., Matrix 4) had a density of about 178.2 $mg/cm^3$; and a fifth synthetic matrix specimen (i.e., Matrix 5) had a density of about 247.0 $mg/cm^3$. A chart depicting the different densities for the five different specimens is set forth below.

|  | Average Density ($mg/cm^3$) | Density Standard Deviation ($mg/cm^3$) |
| --- | --- | --- |
| Matrix 1 | 93.0 | 21.9 |
| Matrix 2 | 120.5 | 20.0 |
| Matrix 3 | 131.2 | 31.5 |
| Matrix 4 | 178.2 | 39.9 |
| Matrix 5 | 247.0 | 32.7 |

Figure 6:
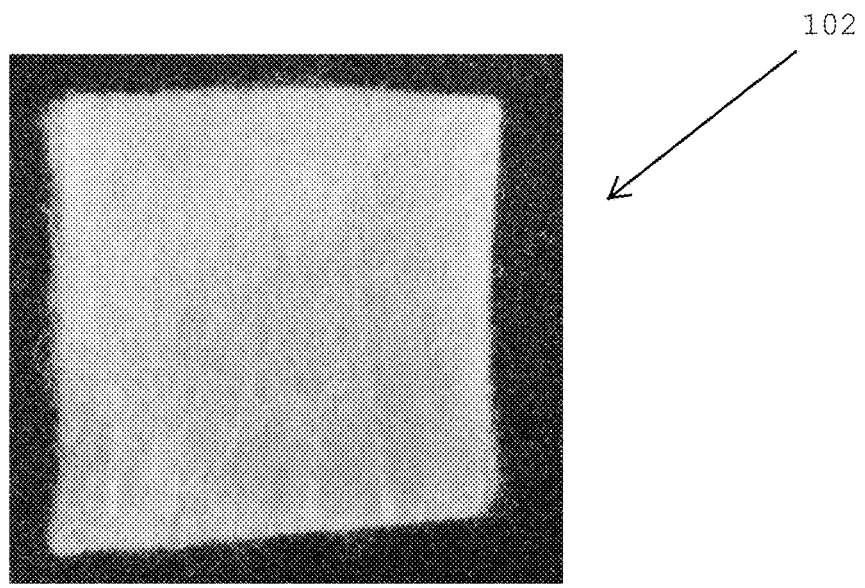
FIG. 6 is a synthetic matrix of a two component sealant used for sealing a resected surface of tissue, in accordance with one embodiment of the present patent application.
Figure 7:
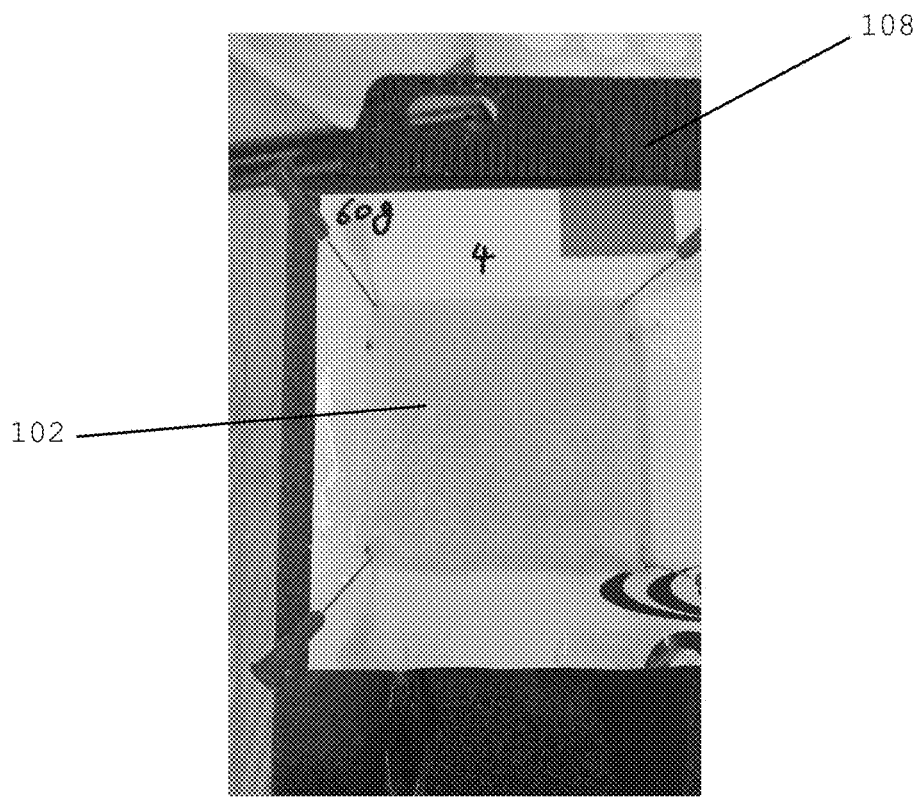
FIG. 7 shows the synthetic matrix of FIG. 6 secured to a 45 degree inclined plane following application of a 10% albumin, 75 mg/ml 4 Arm PEG-SG-10K, 50 mM carbonate (pH=8.0) biological adhesive, in accordance with one embodiment of the present patent application.

Referring to FIGS. 6 and 7, in one embodiment, in order to assess the ability of the different matrices 102 to absorb and retain a biosynthetic adhesive, each matrix was sized to be a 6×6 cm square matrix. In one embodiment, each matrix held on a test board 108 at an approximately 45 degree angle. In one embodiment, a biosynthetic adhesive (i.e., 10% albumin, 75 mg/mL 4 Arm PEG-SG-10k, 50 mM carbonate at pH=8.0) was sprayed onto each 6×6 cm square matrix using a spray device such as an Evicel® Airless Spray Accessory. After being applied to the synthetic matrix 102, the biosynthetic adhesive was allowed to cure for two minutes. Each matrix was assessed to determine the retention of the biosynthetic adhesive by the synthetic matrix and the penetration of the biosynthetic adhesive through the thickness of the synthetic matrix.

In one embodiment, the retention of the biosynthetic adhesive by each of the five synthetic matrix samples (i.e., Matrix 1, Matrix 2, Matrix 3, Matrix 4, and Matrix 5) was measured gravimetrically. In other words, synthetic matrix samples having different densities were studied to evaluate retention of the biosynthetic adhesive. A one-way ANOVA test was used to demonstrate that there were significant differences in permeation and retention at different densities ($p<0.05$). The synthetic matrix specimen (i.e., Matrix 4) having a density of 178.2 $mg/cm^3$ was observed to result in the greatest biosynthetic adhesive retention while the least biosynthetic adhesive retention was observed when testing the synthetic matrix specimen (i.e., Matrix 1) having a density of 93.0 $mg/cm^3$, and the synthetic matrix specimen (i.e., Matrix 5) having a density of 247 $mg/cm^3$. The fourth matrix specimen (i.e., Matrix 4) having a density of 178.2 $mg/cm^3$ represented a 75%, 25%, 23%, and 80% increase in biosynthetic adhesive retention relative to the other specimens at 93.0 $mg/cm^3$ 120.5 $mg/cm^3$, 131.2 $mg/cm^3$, and 247 $mg/cm^3$ conditions, respectively.

In one embodiment, the ability of the biosynthetic adhesive to penetrate or traverse through the synthetic matrix specimens having different densities was assessed via confocal microscopy. In one embodiment, a cross-section of each synthetic matrix was imaged and measured via image processing methods.

Figure 8:
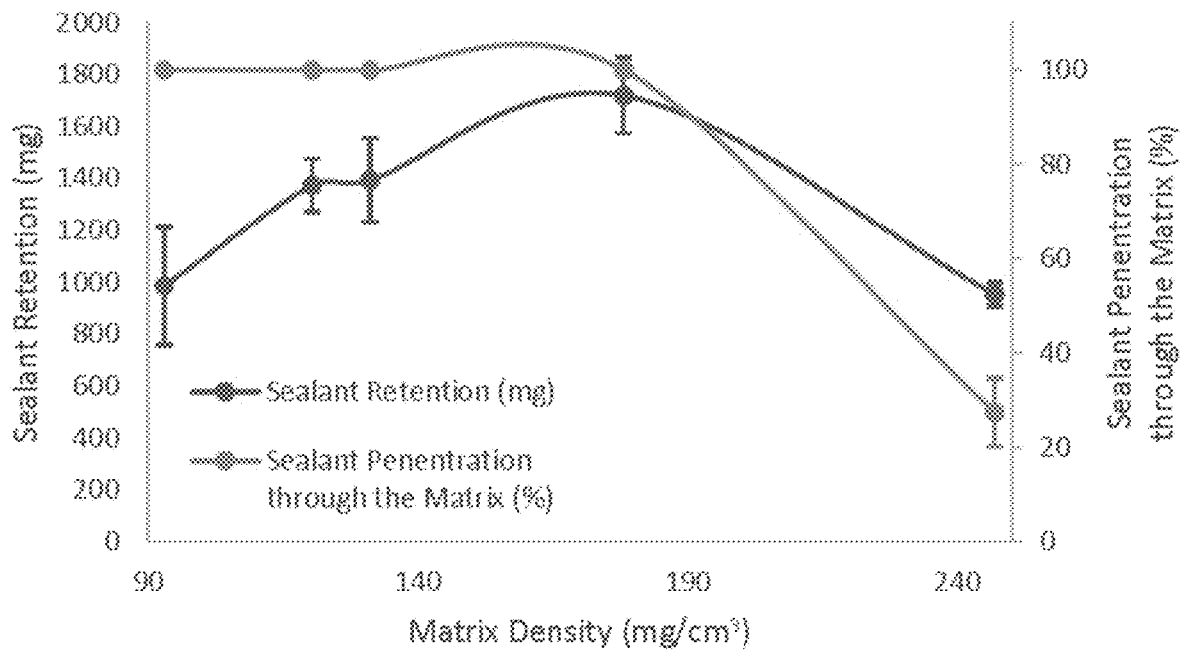
FIG. 8 is a graph that plots the retention and penetration of a biosynthetic adhesive into synthetic matrices having different density levels, in accordance with one embodiment of the present patent application.

The biosynthetic adhesive retention and biosynthetic adhesive penetration data are shown together in FIG. 8. At low matrix densities, the biosynthetic adhesive can completely penetrate through the synthetic matrix. As the density of the matrix increases, there is an increase in the ability of the matrix to absorb the biosynthetic adhesive. At a critical point, however, the matrix density becomes too great to allow the biosynthetic adhesive to completely penetrate through the depth of matrix, and the biosynthetic adhesive can no longer pass completely through the matrix as was the case at lower matrix densities. The inability of the sealant to penetrate through the matrix then decreases the ability of the matrix to retain the sealant, which results in the sealant simply running off the exposed surface of the matrix. Without complete sealant penetration of the matrix, the sealant is unable to bind to the underlying tissue in vivo.

As documented in the graph shown in FIG. 8, a Kruskal-Wallis test demonstrated that there was complete penetration of the biosynthetic adhesive through the fourth synthetic matrix specimen (i.e., Matrix 4) having a matrix density of 178.2 mg/cm³ after which there was a significant 73% drop in penetration through denser synthetic matrices. In the graph shown in FIG. 8, the error bars represent one (1) standard deviation.

Figure 9:
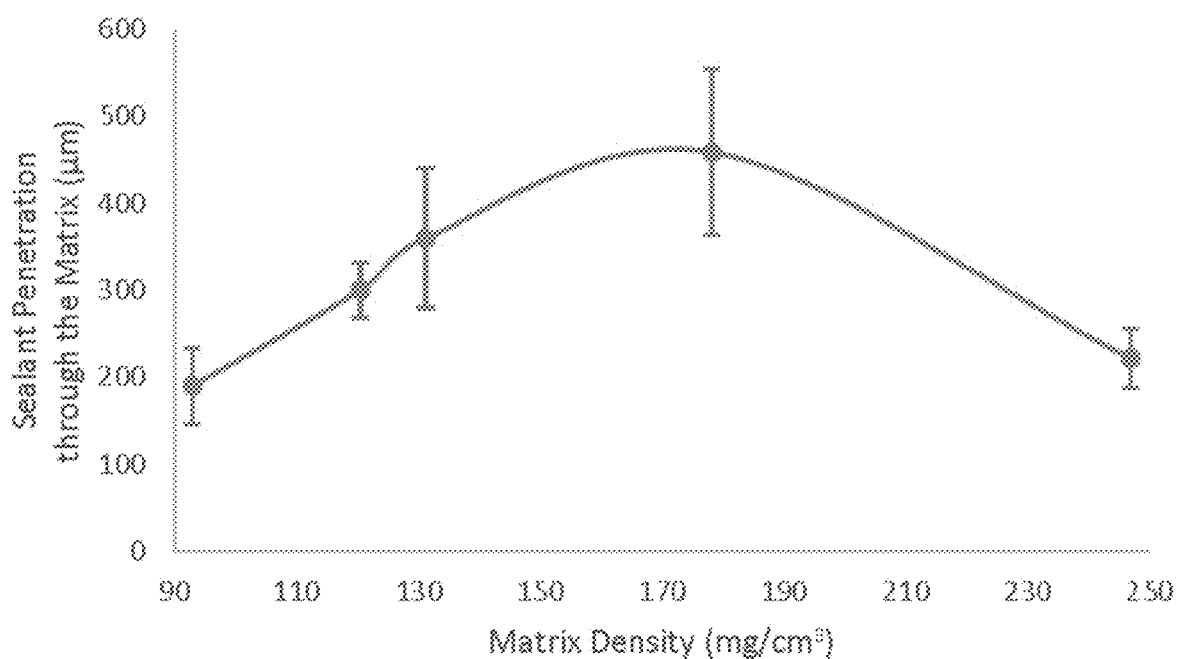
FIG. 9 is a graph that plots the penetration of a biosynthetic adhesive through synthetic matrices having different density levels, in accordance with one embodiment of the present patent application.

FIG. 9 is a graph that shows the penetration of the biosynthetic adhesive through the thickness of the matrix specimens at different matrix densities. Due to the nature of the PG910 matrix, as the density of the matrix increases, there is a corresponding increase in the thickness of the matrix itself. Up to a matrix density of 178.2 mg/cm3, the sealant completely penetrates through the matrix and the thickness of the biosynthetic adhesive increases, as well. Above the matrix density of 178.2 mg/cm3, although the matrix thickness continues to increase, the thickness of the biosynthetic adhesive will dramatically decrease due to poor penetration of the biosynthetic adhesive through the matrix. For example, at a matrix density of 247 mg/cm³, the distance of the biosynthetic adhesive penetration through the matrix is 52% lower than the penetration through a matrix specimen having density of 178.2 mg/cm³. In the graph shown in FIG. 9, the error bars represent one (1) standard deviation.

FIGS. 10-14 shows representative confocal microscopy images of penetration of the biosynthetic adhesive through the thicknesses of five synthetic matrix specimens having different densities. In FIGS. 10-14, the distance between the two red arrows indicates the sealant penetration through the respective matrix.

Figure 10:
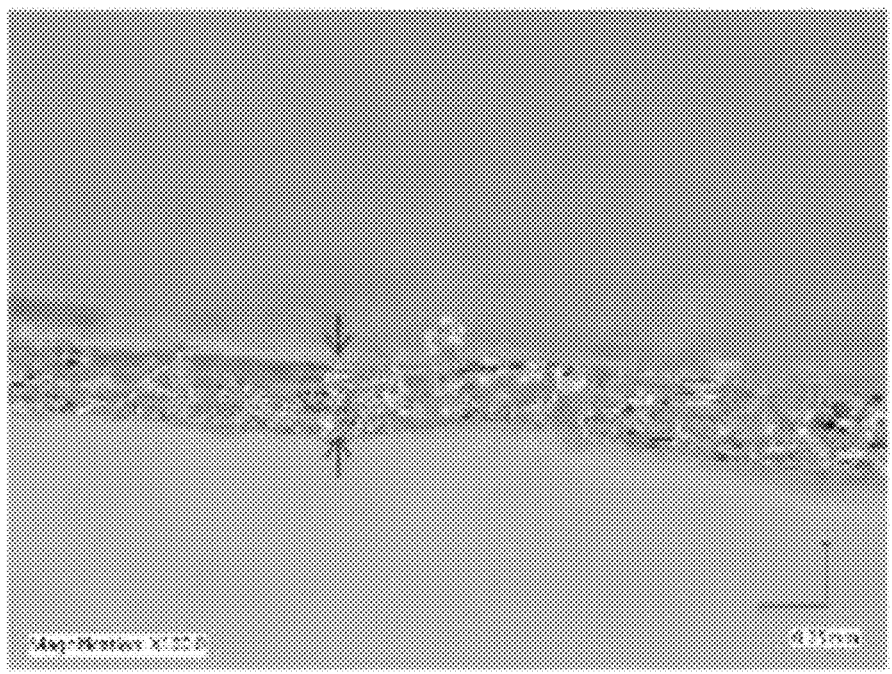
FIG. 10 has two arrows that show the depth of penetration of a biosynthetic adhesive through a first synthetic matrix (Matrix 1) having a density of 93.0 mg/cm$^3$, in accordance with one embodiment of the present patent application.
Figure 11:
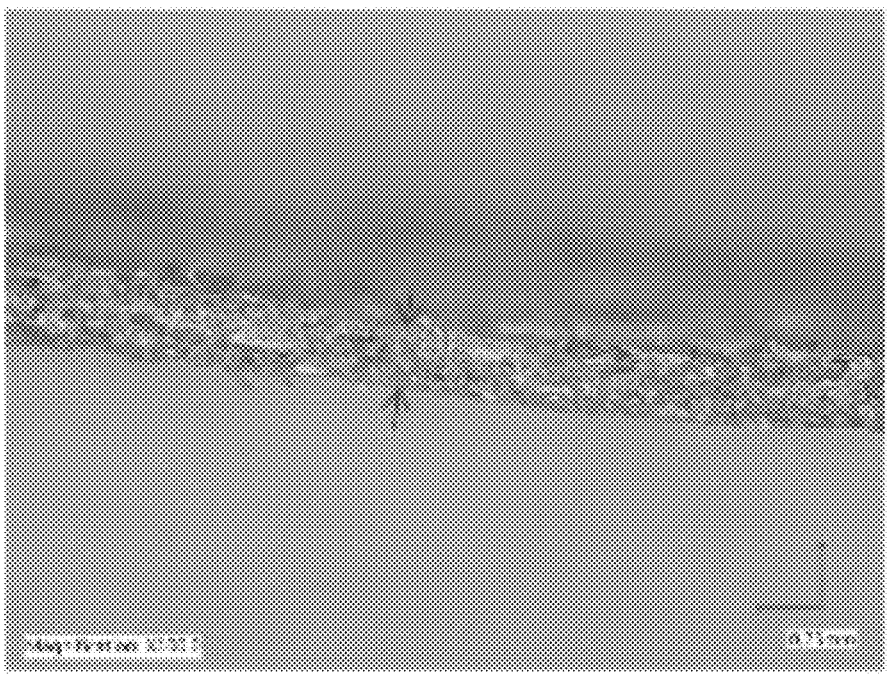
FIG. 11 has two arrows that show the depth of penetration of a biosynthetic adhesive through a second synthetic matrix (Matrix 2) having a density of 120.5 mg/cm$^3$, in accordance with one embodiment of the present patent application.
Figure 12:
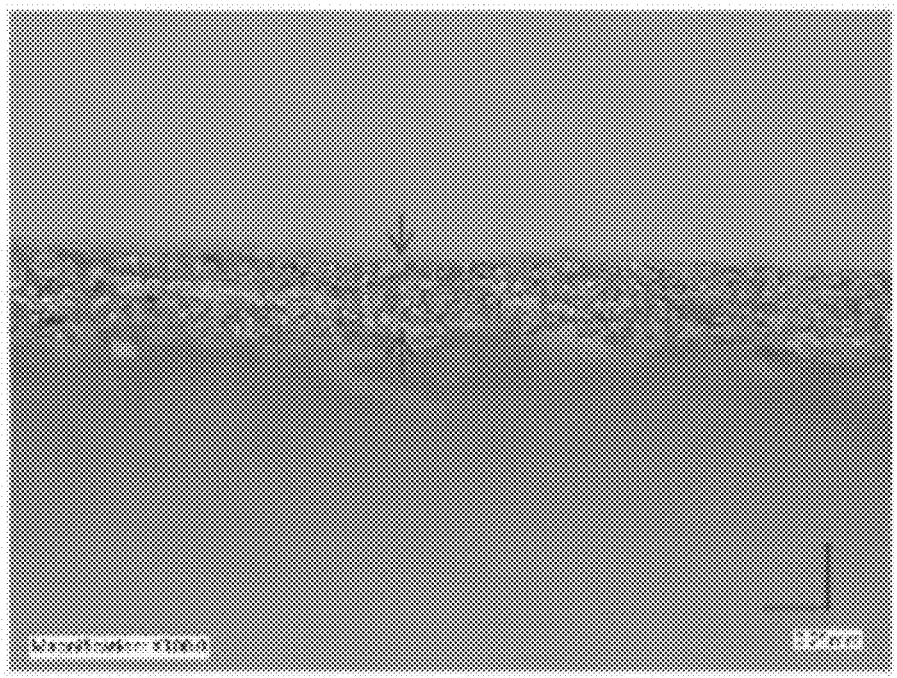
FIG. 12 has two arrows that show the depth of penetration of a biosynthetic adhesive through a third synthetic matrix (Matrix 3) having a density of 131.2 mg/cm$^3$, in accordance with one embodiment of the present patent application.
Figure 13:
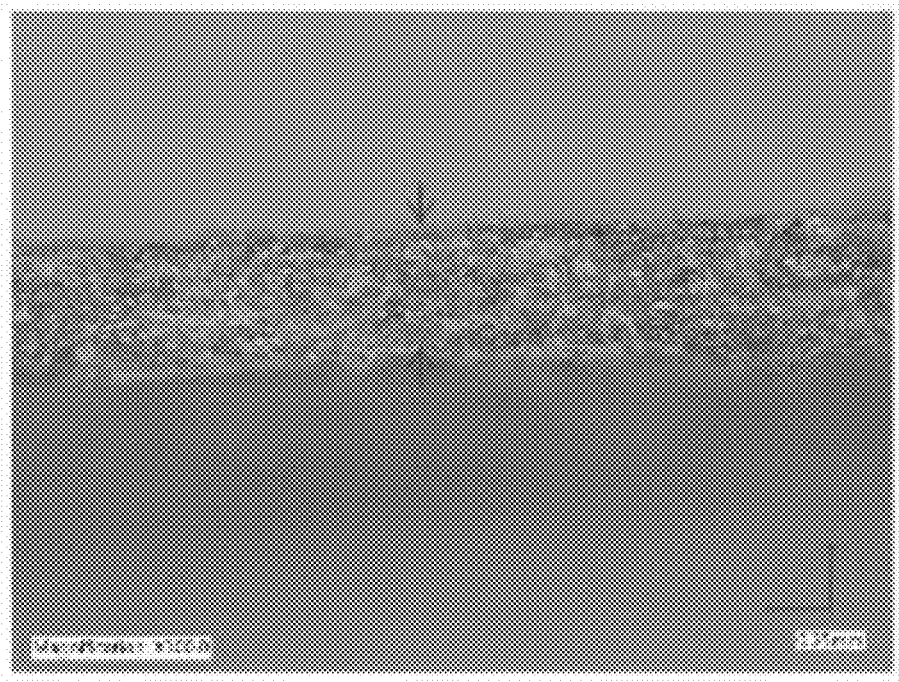
FIG. 13 has two arrows that show the depth of penetration of a biosynthetic adhesive through a fourth synthetic matrix (Matrix 4) having a density of 178.2 mg/cm$^3$, in accordance with one embodiment of the present patent application.
Figure 14:
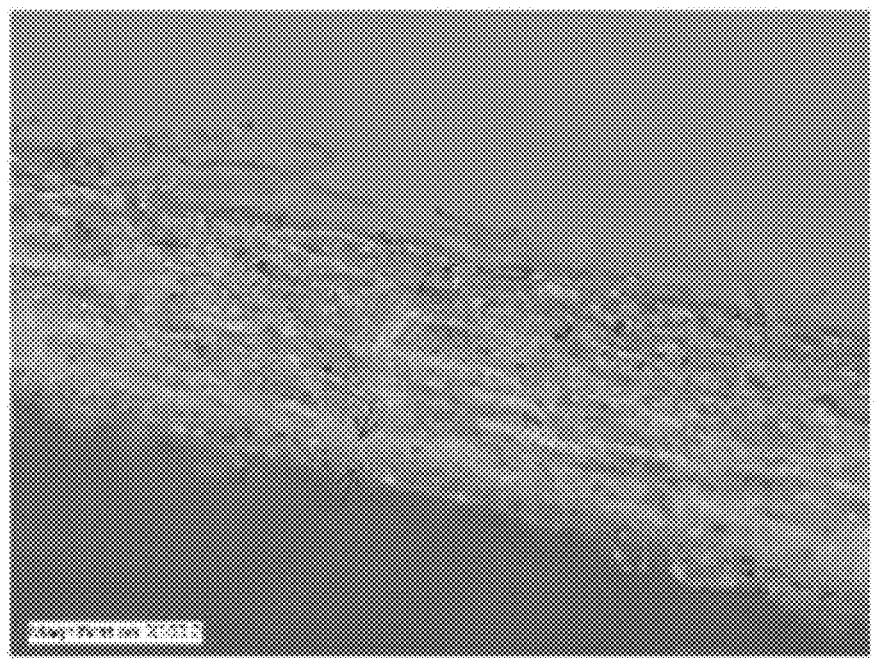
FIG. 14 has two arrows that show the depth of penetration of a biosynthetic adhesive through a fifth synthetic matrix (Matrix 5) having a density of 247.0 mg/cm$^3$, in accordance with one embodiment of the present patent application.

FIG. 10 shows a first matrix specimen (Matrix 1) having a density of 93.0 mg/cm³. FIG. 11 shows a second matrix specimen (Matrix 2) having a density of 120.5 mg/cm³. FIG. 12 shows a third matrix specimen (Matrix 3) having a density of 131.2 mg/cm³. FIG. 13 shows a fourth matrix specimen (Matrix 4) having a density of 178.2 mg/cm³, FIG. 14 shows a fifth matrix specimen (Matrix 5) having a density of 247.0 mg/cm³.

The synthetic matrix specimens having densities of 93.0-178.2 mg/cm³ (i.e., Matrix Specimens 1-4) were completely penetrated by the biosynthetic adhesive. The penetration of the biosynthetic adhesive through the synthetic matrix specimen having a density of 247.0 mg/cm³ (Matrix Specimen 5 shown in FIG. 14) was 52% less than for the synthetic matrix specimen having densities of 178.2 mg/cm³ (Matrix Specimen 4 shown in FIG. 13).

Figure 15:
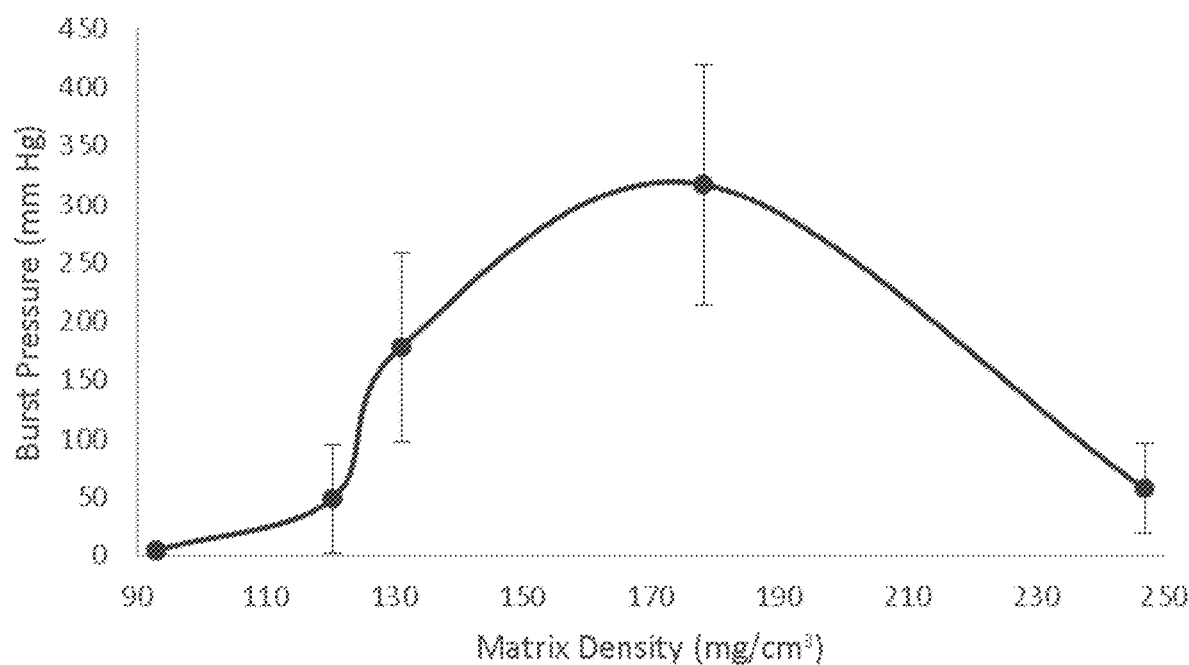
FIG. 15 is a graph that plots the burst pressure levels for synthetic matrices having different density levels, in accordance with one embodiment of the present patent application.

In one embodiment, the functional consequences of the observed differences in retention and penetration of the biosynthetic adhesive were assessed via a benchtop hydraulic burst pressure test. In one embodiment, a synthetic matrix specimen with previously cured biosynthetic adhesive was mounted on the test fixture. Saline was pumped underneath the matrix specimen at a rate of 2 mL/min until failure. The maximum pressure at failure was recorded. Synthetic matrix specimens having the five different density levels disclosed herein were evaluated. Referring to FIG. 15, the synthetic matrix specimen having a density of 178 mg/cm³ (i.e., Matrix 4 shown in FIG. 13) attained a burst pressure of 317 mmHg, which was 73 times greater than the synthetic matrix specimen having a density of 93.0 cm/mg³ (i.e., Matrix 1 in FIG. 10), six (6) times greater than the synthetic matrix specimen having a density of 120.5 cm/mg³ (i.e., Matrix 2 in FIG. 11), 1.78 times greater than the synthetic matrix specimen having a density of 131.2 cm/mg³ (i.e., Matrix 3 in FIG. 12), and five (5) times greater than the synthetic matrix specimen having a density of 247 mg/cm³ (i.e., Matrix 5 in FIG. 14). In the graph shown in FIG. 15, the error bars represent one (1) standard deviation. As a result of testing using the Welch ANOVA test, it was determined that the synthetic matrix specimen having a density of 178 mg/cm³ (i.e., Matrix 4 in FIG. 13) was significantly greater at sealing the resected surfaces of organs than the other synthetic matrix specimens having different densities.

In soft tissue resection, pressures of 9 mm Hg can be expected, however, in one embodiment, a safety factor of 3 is preferably applied to ensure desired performance. In high pressure bleeding, the upper limit of clinical pressures can reach 160 mmHg.

Figure 16:
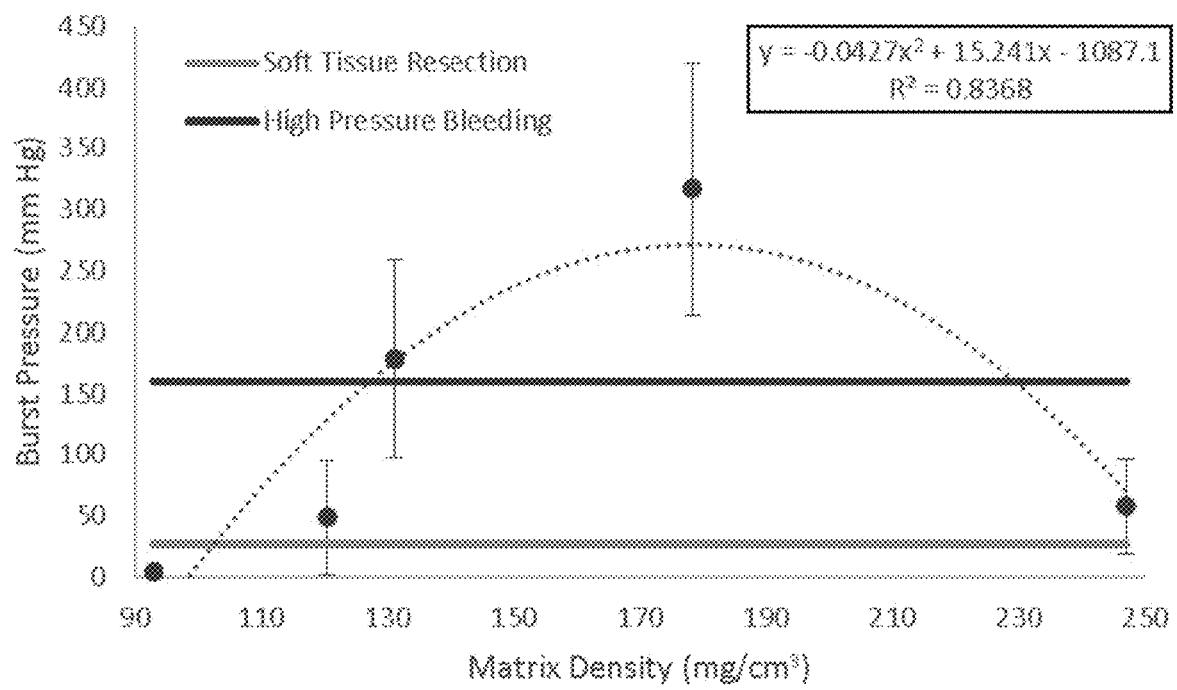
FIG. 16 is a graph that plots the burst pressure levels for synthetic matrices having different density levels for soft tissue resection and high pressure bleeding, in accordance with one embodiment of the present patent application.

Referring to FIG. 16, in order to determine the minimum required matrix density for adequate sealing, a quadratic regression model was generated in Microsoft Excel for the burst pressure data vs. matrix density ($R^2$=83.65%). A response optimizer algorithm in Minitab 18 was employed to determine the minimum matrix density that would result in a burst pressure of 27 mmHg and of 160 mmHg. The minimum matrix density was calculated to be 102.7 mg/cm³ and 128.7 mg/cm³, respectively. In the graph shown in FIG. 16, the error bars represent one (1) standard deviation.

Figure 17:
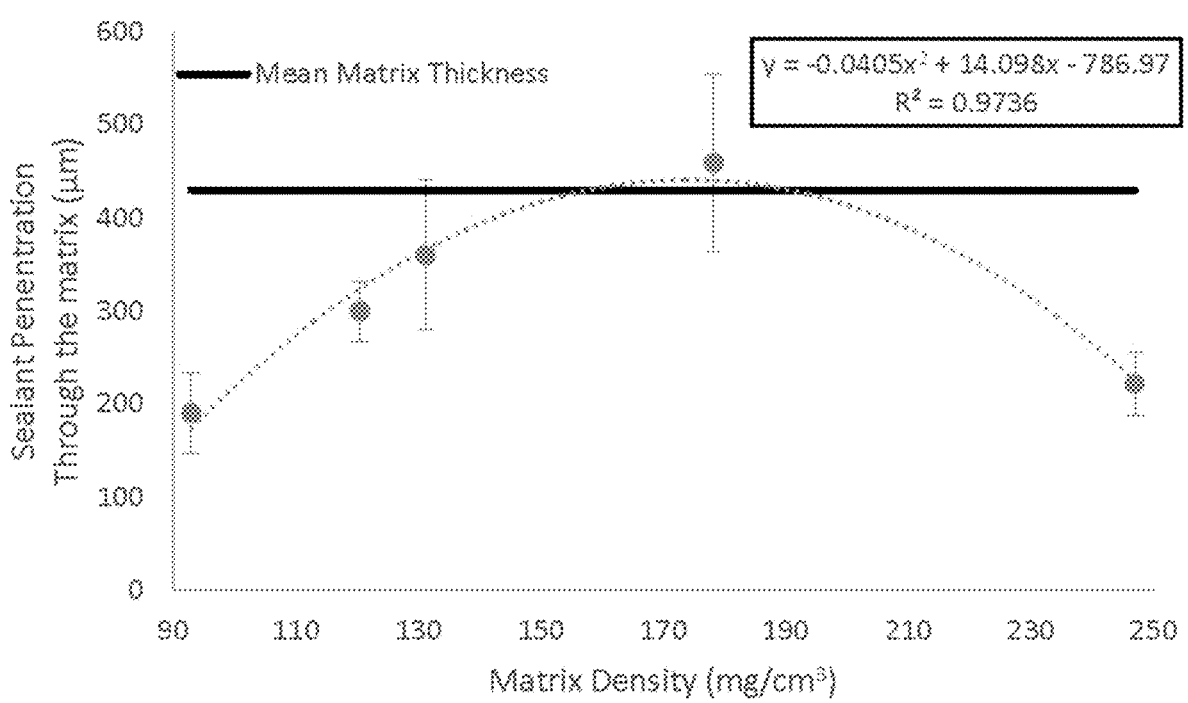
FIG. 17 is a graph that plots the burst pressure levels for synthetic matrices having different density levels, in accordance with one embodiment of the present patent application.

Referring to FIG. 17, the maximum matrix density for adequate sealing is restricted to a density that allows for complete penetration of the biosynthetic adhesive through the thickness of the synthetic matrix. A quadratic regression model was calculated in Microsoft Excel for the sealant thickness data ($R^2$=97.35%). The maximum matrix density was defined as the matrix density that resulted in sealant penetration greater than the average thickness of the matrices tested (i.e., 430 μm). A response optimizer algorithm in Minitab 18 was employed to determine that the maximum matrix density that would result in a biosynthetic adhesive penetration of 430 μm corresponded to a matrix density value of 190.7 mg/cm³. In the graph shown in FIG. 17, the error bars represent one (1) standard deviation.

Therefore, in one embodiment, the optimal matrix density employed for sealing a soft tissue resection is about 102-191 mg/cm³ and more preferably 102.7-190.7 mg/cm³ and the optimal matrix density employed for sealing high pressure bleeding is about 128-191 mg/cm³, and more preferably 128.7-190.7 mg/cm³.

To demonstrate that a synthetic matrix at the selected density works properly to seal a resected surface, a synthetic matrix specimen having a density of 107.9 mg/cm³ was used on a liver partial lobe resection and showed that it is effective in reaching hemostasis.

Figure 18A:
FIG. 18A shows a method of resecting a liver, in accordance with one embodiment of the present patent application.
Figure 18B:
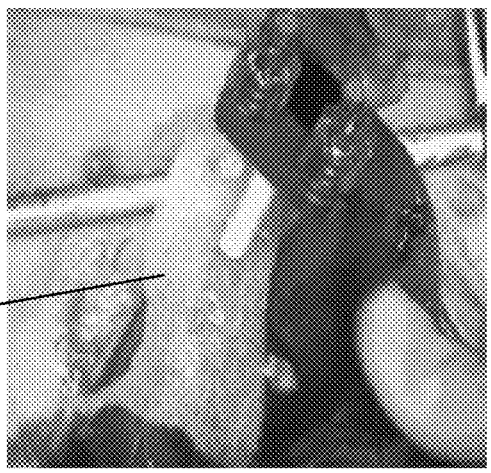
FIG. 18B shows a method of placing a synthetic matrix over a resected surface of the liver shown in FIG. 18A, in accordance with one embodiment of the present patent application.
Figure 18C:
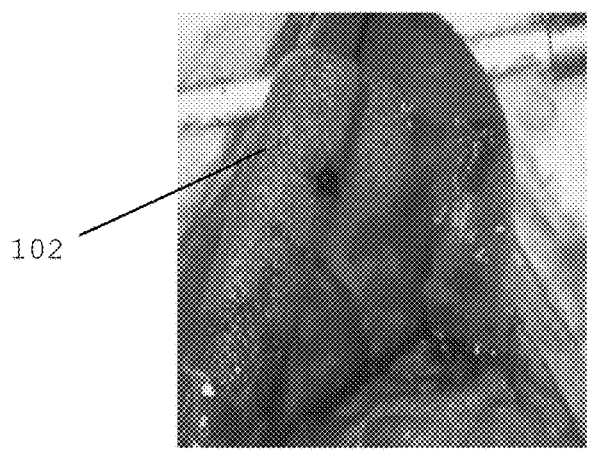
FIG. 18O shows the synthetic matrix of FIG. 18B after a biosynthetic adhesive has been applied to the synthetic matrix for sealing the resected surface of the liver shown in FIG. 18A, in accordance with one embodiment of the present patent application.

Referring to FIG. 18A, in one embodiment, a liver undergoes a partial lobe resection. Referring to FIGS. 18B and 18C, a synthetic matrix 102 having a density of 107.9 mg/cm³ and a biosynthetic adhesive are applied on the partial lobe resection of the liver using the systems, devices and methods disclosed herein. The combination of the synthetic matrix and the biosynthetic adhesive sealed the resected surface, prevented bleeding and fluid leaks, and reached hemostasis.

In one embodiment, a sealant including a synthetic mesh and a biosynthetic adhesive are applied together onto a resected surface of a soft organ. The synthetic mesh and the biosynthetic adhesive may be applied in different forms and methods as described below in order to control bleeding, fluid leaks, and air leaks.

In one embodiment, a biodegradable synthetic matrix (e.g., a VICRYL® non-woven PG910) is placed on a resected surface followed by application of a biosynthetic adhesive (e.g., albumin and PEG-SG adhesive solution) on top of the synthetic PG910 mesh. Following one to five minutes, the synthetic matrix and biosynthetic adhesive combination preferably forms a sealant at the resected surface.

In one embodiment, a biosynthetic adhesive (e.g., in liquid form) may be applied to a synthetic matrix and the synthetic matrix is then applied to the resected tissue.

In one embodiment, a biosynthetic adhesive (e.g., in liquid form) may be applied to the resected tissue and the synthetic matrix is then applied to the resected tissue and contacts the pre-applied biosynthetic adhesive.

In one embodiment, after the synthetic matrix is placed onto the resected surface, additional biosynthetic adhesive may be applied onto the placed synthetic matrix.

In one embodiment, PEG-SG (and possibly also albumin) is pre-coated on the synthetic matrix (e.g., a VICRYL® PG910 mesh) and the synthetic matrix is applied dry on wet resected tissue to achieve sealing.

In one embodiment, the PEG-SG and albumin components of the biosynthetic adhesive are applied to the resected tissue as a powder mixture followed by placement of a dry synthetic matrix (e.g., a VICRYL® PG910 mesh) on a wet resected tissue to achieve sealing. Dry storage preferably enables longer term storage of the product at room temperature. In certain preferred embodiments, the powder mixture may have the following ratios of PEG-SG to protein (albumin): 0/100%, 20/80%, 40/60%, 50%50, 60/40%, 80/20% and 100/0% PEG-SG to albumin, respectively.

In one embodiment, the PEG-SG may be pre-coated on the synthetic substrate (e.g., the VICRYL® PG910 mesh), and the albumin solution may be applied to the synthetic matrix and/or the resected tissue, and the synthetic matrix may be applied immediately to the resected tissue to achieve sealing.

In another embodiment, the mesh can be used as a buttress material for linear staple with wide edges (wider than the linear anvil; as described in Disclosure #150334 Design of stapler anvil for delivery of buttress material wider than the anvil width) followed by application of fluid adhesive on the mesh to provide sealing of exposed tissue (during soft organ resection using linear stapler, for example)

Example 1. Use of the Synthetic Matrix and the Biosynthetic Adhesive as a Sealant in a Porcine Model of Liver Resection. The systems, devices and methods disclosed herein were used as a sealant in a porcine model of liver resection as follows. The liver lobe was resected using a surgical scalpel and the liver was clamped to minimize blood flow to the resected lobe. A biosynthetic adhesive solution was prepared as follows: a dual syringe system (e.g., Evicel device) holding 5 ml in each syringe of 1) 20% albumin solution, and 2) 150 mg/ml of PEG-SG solution. The content of the two syringes was mixed in the spray tip of the device as it was sprayed onto the resected liver surface (e.g., about 5 ml). Then, the synthetic mesh (e.g., non-woven VICRYL® PG910 mesh) was placed on the resected surface. The synthetic matrix preferably conforms to the geometry of the resected tissue. Additional biosynthetic adhesive (e.g., about 5 ml) was sprayed on the synthetic matrix with no pressure applied to the synthetic matrix. After two minutes, the clamp was removed to restore normal blood flow to the resected lobe. No bleeding or fluid leaks from the resected surface were visually observed. After the adhesive cures, sutures may be passed through the cured sealant device (i.e., a combination of the synthetic mesh and the cured adhesive) to help secure the sealant device to the resected organ. The cured sealant device may serve as a buttress to reduce stress around the suture holes. Following several minutes, the sealant was removed, which required significantly high force due to strong adhesion of the synthetic matrix and the biosynthetic adhesive to the resected tissue and re-bleeding was observed. The Example 1 study demonstrates the efficiency of the sealing systems, devices and methods disclosed herein and its superiority over other tested matrices with the same adhesives.

Figure 19A:
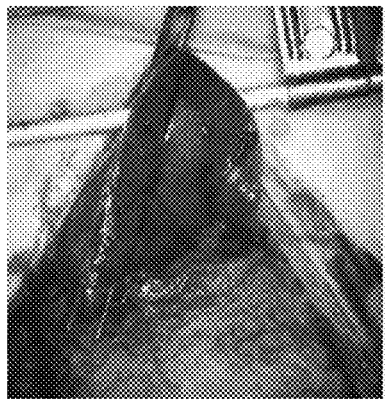
FIG. 19A shows a first stage of a surgical method including resecting a liver lobe, in accordance with one embodiment of the present patent application.
Figure 19B:
FIG. 19B shows a second stage of a surgical method including spraying a biosynthetic adhesive onto the resected surface of the liver lobe, in accordance with one embodiment of the present patent application
Figure 19C:
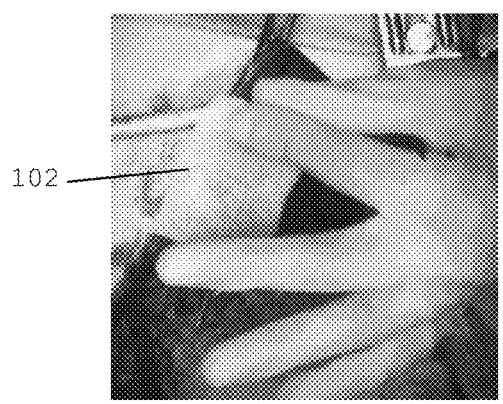
FIG. 19O shows a third stage of a surgical method including placing a synthetic matrix over the sprayed, resected surface of the liver lobe, in accordance with one embodiment of the present patent application
FIG. 19D shows the synthetic matrix of FIG. 19O after being sprayed with the biosynthetic adhesive sealant.
FIG. 19E shows a curing stage for the biosynthetic adhesive.
FIG. 19F shows another stage of a surgical method including removing a clamp and re-establishing blood flow to the resected liver lobe, in accordance with one embodiment of the present patent application
FIG. 19G shows the resected surface of the liver lobe after the synthetic matrix has been peeled away to demonstrate that bleeding will recommence if the synthetic matrix is removed from the resected surface of the liver lobe.
Figure 19D:
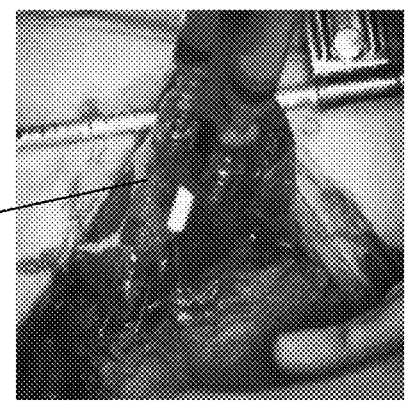
Figure 19E:
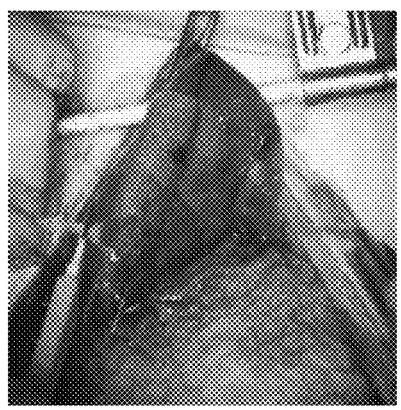
Figure 19F:
Figure 19G:

FIGS. 19A-19G show the implementation of Example 1 including the PG910 Mesh and Liquid albumin/PEG-SG adhesive combination being used as a sealant in a porcine model of liver resection. FIG. 19A shows a resected surface and clamped liver lobe. FIG. 19B shows the adhesive sealant being sprayed onto the resected surface. FIG. 19C shows the synthetic matrix 102 (e.g., VICRYL® PG910 mesh) being placed on the sprayed resected surface. FIG. 19D shows the synthetic matrix 102 after being sprayed with the biosynthetic adhesive sealant. FIG. 19E shows the two minutes waiting period for enabling the biosynthetic adhesive to cure. FIG. 19F shows clamp removal and re-establishment of blood flow to the resected lobe, whereby no bleeding is observed in the treated areas. Following sealant polymerization, the VICRYL® mesh combined with albumin/PEG-SG demonstrated sufficient efficacy as a sealant. FIG. 19G shows the resected surface after the sealant has been peeled away, which results in additional bleeding from the resected surface.

Example 2. Use of the sealant system during a solid tumor resection procedure. In a lung tumor resection procedure, the sealant system is used for patients undergoing a pulmonary resection. Immediately following tumor resection in the operating room, a sealing system including a synthetic matrix and a biosynthetic adhesive was placed at the areas of risk of leaks (e.g., a staple line, raw and denuded pleura surfaces) to achieve sealing at the resected area(s). The sealing system was applied to the resected organ using laparoscopic and non-laparoscopic methods. Studies demonstrated the efficacy of the synthetic matrix and biosynthetic adhesive combination in sealing pulmonary air leaks, as compared to other matrices used with fibrin glue.

In one embodiment, the sealing systems, devices and methods disclosed herein utilize a two component sealant including a synthetic matrix and a biosynthetic adhesive. The two component sealant provides surgeons with more flexibility in sealing resected tissue by enabling surgeons to apply a biosynthetic adhesive on both a synthetic matrix and/or the resected tissue prior to placing the synthetic matrix on the resected tissue. In one embodiment, after the synthetic matrix has been positioned over the resected tissue, supplemental biosynthetic adhesive may be applied at specific locations, as needed.

In one embodiment, the synthetic matrix of the two component sealing system is flexible for conforming to uneven surfaces, such as an uneven resected surface of an organ.

In one embodiment, the synthetic matrix provides enhanced structural support (i.e., scaffolding) that is substantially greater than that which can be attained by using a liquid sealant by itself.

In one embodiment, the two component sealing system is designed to seal resected surfaces for preventing and/or controlling bleeding, fluid leaks and air leaks.

The sealing system disclosed herein is independent of a patient's clotting system. Thus, surgeons can attain hemostasis and sealing independent of the patient's coagulation status, which could be impaired in patients being resected since most clotting proteins are produced in the liver. The sealing system may also be used for patients on antiplatelet and anticoagulant therapy, e.g., aspirin, heparin or warfarin.

In one embodiment, the two component sealing system is clear and allows surgeons to visually examine the resected surface following sealing. Surgeon visibility and confirmation that treatment is effective is critical and cannot be achieved with opaque liquid sealants and/or opaque patches. In one embodiment, the sealant clarity may reduce the likelihood of iatrogenic injury due to poor visualization at the resection site.

In one embodiment, the two component dealing system disclosed herein preferably provides strong adhesion to resected tissue, however, the synthetic matrix may be manually removed and repositioned, if necessary, for forming a proper seal. In one embodiment, the combination of the synthetic matrix and the biosynthetic adhesive provide strong adhesion to resected tissue through direct covalent bonding with proteins on the tissue surface.

In one embodiment, the two component sealing system enables the properties of the respective components of the system to be modified to optimize retention of the biosynthetic adhesive by the synthetic matrix, and penetration of the biosynthetic adhesive through the thickness of the synthetic matrix. As a result, the specific formulations of the biosynthetic adhesive and the synthetic matrix may be modified to allow for specific characteristics (e.g., degradation rate, strength).

In one embodiment, the adhesive may include a synthetic adhesive. In one embodiment, the adhesive may include a biocompatible, reactive electrophile and a nucleophile. In one embodiment, the electrophile may include PEG-SG. In one embodiment, the nucleophile may be selected from any source of $NH_2$ group, any appropriate protein or protein mixture, albumin, polyethylene glycol amines (PEG-$NH_2$), and combinations of albumin and PEG-$NH_2$.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of sealing a resected surface of an organ comprising:
    applying a synthetic matrix to a resected surface of an organ;
    applying an adhesive on said synthetic matrix so that said adhesive penetrates through interstices of said synthetic matrix for contacting an interface between said synthetic matrix and the resected surface of said organ; and
    curing said adhesive for bonding said synthetic matrix to the resected surface of said organ,
    wherein said synthetic matrix comprises fibers and has a density range of 102.7-190.7 mg/cm$^3$.

2. The method as claimed in claim 1, wherein said synthetic matrix is a biodegradable, porous, flexible substrate.

3. The method as claimed in claim 1, wherein said synthetic matrix comprises a non-woven mesh made of polyglactin 910.

4. The method as claimed in claim 1, wherein said synthetic matrix and said adhesive are at least partially transparent.

5. The method as claimed in claim 1, wherein said synthetic matrix comprises fibers and has a density range of 128.7-190.7 mg/cm$^3$.

6. The method as claimed in claim 1, wherein said adhesive comprises a biosynthetic adhesive or a synthetic adhesive.

7. The method as claimed in claim 6, wherein said biosynthetic adhesive comprises a partially hydrolyzed protein and PEG-SG.

8. The method as claimed in claim 7, wherein said partially hydrolyzed protein comprises albumin.

9. The method as claimed in claim 8, wherein said biosynthetic adhesive comprises a mixture of a 10% albumin solution and 75 mg/ml of PEG-SG solution.

10. The method as claimed in claim 1, wherein said adhesive comprises a biocompatible, reactive electrophile and a nucleophile.

11. The method as claimed in claim 10, wherein said electrophile comprises a polyethylene glycol succinimidyl glutarate ester (PEG-SG).

12. The method as claimed in claim 11, wherein said nucleophile is selected from the group consisting of any source of amine ($NH_2$) groups, any appropriate protein or protein mixture, albumin, polyethylene glycol amines (PEG-$NH_2$), and combinations of albumin and PEG-$NH_2$.

13. The method as claimed in claim 1, wherein said adhesive is in a liquid or powder form and is cross-linked with fibers of said synthetic matrix.

14. A method of sealing a resected surface of an organ comprising:
    applying a porous, bioabsorbable synthetic matrix made of polyglactin 910 to a resected surface of an organ;
    applying an adhesive on said synthetic matrix so that said adhesive penetrates through pores of said synthetic matrix for contacting an interface between said synthetic matrix and the resected surface of said organ; and
    curing said adhesive for bonding said synthetic matrix to the resected surface of said organ,
    wherein said synthetic matrix comprises fibers and has a density range of 102.7-190.7 mg/cm$^3$.

15. The method as claimed in claim 14, wherein said adhesive is a biosynthetic adhesive or a synthetic adhesive.

16. The method as claimed in claim 14, wherein said cured adhesive is cross-linked with said fibers of said synthetic matrix.

17. The method as claimed in claim 14, wherein said synthetic matrix comprises fibers and has a density range of 128.7-190.7 mg/cm$^3$, and wherein said cured adhesive is cross-linked with said fibers of said synthetic matrix.

18. The method as claimed in claim 14, further comprising:
    prior to the applying a porous, bioabsorbable synthetic matrix step, pre-applying said adhesive on the resected surface of said organ.

19. A kit for sealing a resected surface of an organ comprising:
    a synthetic matrix comprising a non-woven mesh made of polyglactin 910;
    an adhesive comprising a biocompatible, reactive electrophile and a nucleophile,
    wherein said synthetic matrix is porous and has a density range of 102.7-190.7 mg/cm$^3$.

20. The kit as claimed in claim 19, wherein said adhesive is a biosynthetic adhesive comprising a partially hydrolyzed protein and PEG-SG.

21. The kit as claimed in claim 20, further comprising:
a dual syringe for dispensing said biosynthetic adhesive including a first syringe barrel and a second syringe barrel;
said first syringe barrel containing a 20% albumin solution; and
said second syringe barrel containing a 150 mg/ml of PEG-SG solution.

22. The method as claimed in claim 19, wherein said synthetic matrix is porous and has a density range of 128.7-190.7 mg/cm$^3$.

23. The kit as claimed in claim 19, wherein said adhesive is in liquid or powder form.

* * * * *